United States Patent
Jabour et al.

(10) Patent No.: US 11,035,764 B2
(45) Date of Patent: Jun. 15, 2021

(54) EXTRACTION OF MYCOTOXINS

(71) Applicant: Charm Sciences, Inc., Lawrence, MA (US)

(72) Inventors: John Jabour, Farmington, NH (US); Steven J. Saul, Arlington, MA (US); Mark E. Tess, Merrimack, NH (US)

(73) Assignee: Charm Sciences, Inc., Lawrence, MA (US)

( * ) Notice: Subject to any disclaimer, the term of this patent is extended or adjusted under 35 U.S.C. 154(b) by 58 days.

(21) Appl. No.: 14/372,088

(22) PCT Filed: Feb. 4, 2013

(86) PCT No.: PCT/US2013/024650
§ 371 (c)(1),
(2) Date: Jul. 14, 2014

(87) PCT Pub. No.: WO2013/116847
PCT Pub. Date: Aug. 8, 2013

(65) Prior Publication Data
US 2014/0356978 A1    Dec. 4, 2014

Related U.S. Application Data

(60) Provisional application No. 61/618,245, filed on Mar. 30, 2012, provisional application No. 61/594,433, filed on Feb. 3, 2012.

(51) Int. Cl.
*G01N 1/34* (2006.01)
*G01N 33/543* (2006.01)
*G01N 33/569* (2006.01)
*G01N 33/10* (2006.01)
*G01N 1/40* (2006.01)

(52) U.S. Cl.
CPC ............. *G01N 1/34* (2013.01); *G01N 1/4055* (2013.01); *G01N 33/10* (2013.01); *G01N 33/54366* (2013.01); *G01N 33/56961* (2013.01); *G01N 2001/4061* (2013.01); *G01N 2333/37* (2013.01); *Y10T 436/25375* (2015.01)

(58) Field of Classification Search
None
See application file for complete search history.

(56) References Cited

U.S. PATENT DOCUMENTS

| | | | | |
|---|---|---|---|---|
| 4,992,383 A | * | 2/1991 | Farnsworth | C07K 1/128 435/6.12 |
| 5,670,381 A | * | 9/1997 | Jou | G01N 33/558 436/518 |
| 6,057,160 A | * | 5/2000 | Silber | G01N 27/44726 436/501 |
| 6,482,601 B1 | * | 11/2002 | Nasir | G01N 21/6445 435/341 |
| 2002/0004478 A1 | * | 1/2002 | Danko | A61K 38/30 514/8.5 |
| 2002/0197741 A1 | * | 12/2002 | Sabucedo | G01N 33/6887 436/526 |
| 2006/0275841 A1 | * | 12/2006 | Blankfard | G01N 1/4077 435/7.5 |
| 2007/0293416 A1 | * | 12/2007 | Markel | A23L 3/34 424/251.1 |
| 2008/0176957 A1 | * | 7/2008 | Joerger | A61K 8/06 514/738 |
| 2009/0081808 A1 | * | 3/2009 | Burmeister | G01N 21/6428 436/501 |
| 2009/0098560 A1 | * | 4/2009 | Danks | C12N 15/1017 435/6.12 |
| 2009/0246756 A1 | * | 10/2009 | Blondal | C12N 9/16 435/6.11 |
| 2010/0285610 A1 | * | 11/2010 | Saul | G01N 33/558 436/501 |

OTHER PUBLICATIONS

Cookman and Glatz, Extraction of protein from distiller's grain, Bioresource Technology, 100, (2009), p. 2012-2017.*
Bioresource Technology, 100, (2009), p. 2012-2017 and as is evidenced by National Center for Biotechnology Information. Aflatoxin. PubChem Compound Database; CID=186907, https://pubchem.ncbi.nlm.nih.gov/compound/186907 (accessed Aug. 17, 2017). (1 page).*
National Center for Biotechnology Information. Ochratoxin. PubChem Compound Database; CID=442530, https://pubchem.ncbi.nlm.nih.gov/compound/442530 (accessed Aug. 17, 2017), (1 page).*
National Center for Biotechnology Information. Fumonisin. PubChem Compound Database; CID=2733487, https://pubchem.ncbi.nlm.nih.gov/compound/2733487 (accessed Aug. 17, 2017), (1 page).*
Garcia et al., Mycotoxins in Corn Distillers Grains A Concern in Ruminants?, Extension Extra. Paper 135. (2008), 4 pages (Year: 2008).*

* cited by examiner

*Primary Examiner* — Ellen J Marcsisin
(74) *Attorney, Agent, or Firm* — MacCord Mason PLLC

(57) ABSTRACT

A method and composition for extracting an analyte from a test sample such as grain, so as to determine whether the test sample is contaminated with a toxin. The method is particularly useful for detecting the presence in a batch of grain of a mycotoxin, such as for example aflatoxin, ochratoxin, T2, zearalanone, vomitoxin (deoxynivalenol a/k/a DON), patulin and fumonisin. Extraction is performed with use of a composition that includes a proteinaceous material, such as albumin, as an extraction agent.

24 Claims, No Drawings

_EXTRACTION OF MYCOTOXINS_

REFERENCE TO PRIOR APPLICATIONS

This application is the national stage of International Application No. PCT/US2013/024650, filed Feb. 4, 2013, which claims the benefit of U.S. Provisional Application No. 61/618,245, filed Mar. 30, 2012 (hereby incorporated by reference) and U.S. Provisional Application No. 61/594,433, filed Feb. 3, 2012 (hereby incorporated by reference).

BACKGROUND

The technical field of the invention relates to methods of extracting analytes, for example mytoxins, from a sample, such as, for example, grain, or, for example, maize.

Tests to detect one or more analytes in samples are known in the art. Some examples are described in U.S. Pat. No. 5,985,675, issued Nov. 16, 1999; U.S. Pat. No. 6,319,466, issued Nov. 20, 2001; U.S. Pat. No. 7,410,808, issued Aug. 12, 2008; International Publication Number WO 2006/089027, filed Feb. 16, 2006; U.S. Pat. No. 7,785,899, issued Aug. 31, 2010; U.S. Pat. No. 7,863,057, issued Jan. 4, 2011 and International Patent Application Number PCT/US10/39113, filed Jun. 18, 2010 the teachings of all of which are incorporated herein by this reference.

When chromatographic test strips, such as lateral flow test strips, are the testing medium, many sample matrices, such as solid or granular materials, require extraction of analyte into a liquid matrix prior to testing. For example, corn can be ground and the ground sample extracted with various combinations of solvents. Typical solvents include 70% methanol in a 2:1 ratio (2 milliliter per 1 gram of sample) and acetonitrile, ethanol or other concentrations of methanol, for example at 50%, 60%, or 80%. Depending on the use, such solvents can be relatively hazardous and costly. In addition, such solvents may require further dilution or buffering prior to application to a chromatographic medium or other testing medium, such as when using certain chromatographic test strips. Dilution can affect test sensitivity and, therefore, when higher sensitivity is desired, such as in jurisdictions, such as the European Union, which require higher sensitivity to certain toxins as compared to, for example, the United States, dilution can be undesirable. The solvent also may require adjustment depending on either or both the particular matrix from which the analyte is being extracted and the particular analyte being extracted and detected. That is, one solvent may not be a "one size fits all" but, instead require adjustment/optimization depending on the matrix and/or analyte of detection. We describe herein methods and compositions for performing relatively non-hazardous extractions of a variety of toxins, such as mycotoxins, from a sample. Examples of such non-hazardous extraction compositions include a variety of high ionic strength compositions, including those with relatively abundant amine and carboxyl groups, such as protein, amino acid and polyethylene glycol based compositions.

SUMMARY

Aspects include a method for detecting an analyte, such as one or more mycotoxins, for example aflatoxin, ochratoxin, T2, zearalanone, vomitoxin (deoxynivalenol a/k/a DON), patulin and fumonisin, or other of a variety of mycotoxins and other toxins in a sample. The steps of the method can include: extracting the analyte from the sample to form an extract, the extracting including contacting the sample with a composition that includes substances with high ionic strength including substances with abundant amine and/or carboxyl groups such as amino acids and a variety of proteins (the extraction composition); contacting the extract with a labeled receptor to form a mobile phase, the labeled receptor characterized by an ability to bind to the analyte to provide, in the mobile phase, a labeled receptor-analyte complex and further characterized by an ability to provide a detectable signal when the labeled receptor is captured on a solid support; contacting the mobile phase with a first test area on a solid support, the first test area comprising a first test area capture agent immobilized on the solid support, said first test area capture agent configured to both capture labeled receptor unbound by the analyte from the sample and not capture the labeled receptor-analyte complex; and measuring the intensity of the detectable signal at the first test area, wherein the intensity of the detectable signal is related to the concentration of the analyte in the sample. The extraction composition can be provided to a user in a solution or can be in a solid form such as tablet, powder or other solid forms that can be dissolved in, for example, water. When provided to the user in tablet or powder form, for example, with instructions to add water or other available solvent, costs are reduced by the lowering of shipping weight. In addition, longer shelf life may be achieved when maintained in non-liquid form until prior to use. Aspects include mixing the dry extraction composition with a dry sample and adding a solvent, such as water, to the mixture to perform the extraction. After adding the solvent, the mixture can be shaken followed by allowing the solids to settle before utilizing the liquid layer (containing the extracted analyte if present) for testing.

When the extraction composition has been previously dissolved in liquid, the pH can be in the range of between pH 6 and pH 8.5. In one example a protein solution, including 2%-10%, for example, 5% protein, in buffered solution, for example 20 mM sodium phosphate at pH 7.2, was used. In another examples 0.2 M amino acid solution, for example 0.2M arginine in water, at pH 7.2 were used.

Useful as an extraction agent is a composition that includes a proteinaceous material, which is understood to be a material or substance containing one or more proteins or fragments or constituents thereof, such as amino acids or digested components of proteins. Examples of proteinaceous materials include, alone or in combination, bovine collagen, bovine serum albumin, gelatin peptone, soy peptone, soy/casein, a digestive protein, and an enzymatic digest of proteins, e.g., Primatone® or Primatone® RL (a registered trademark of Kerry Group Services Ltd., Tralee County Kerry Ireland). Additional examples of useful proteinaceous materials include proteinaceous materials that are rich in amine and carboxyl groups, where by 'rich' is meant that the proteinaceous material contains a higher concentration of amine or carboxyl groups than the average concentration of such groups in proteins generally. Examples of useful amino acids include, alone or in combination, glycine and arginine.

Aspects include a chromatographic test strip, such as a chromatographic lateral flow test strip, such as a chromatographic lateral flow test strip including nitrocellulose and/or POREX® (Porex is a registered trademark of Porex Technologies Corp., Fairburn, Ga.), as a test medium, as the solid support. The test strip can include a test medium, for example a stationary phase membrane in contact or contacted with the mobile-phase composition and having a first end and a second end, wherein the membrane allows lateral capillary flow of the sample from the first end to the second end and has the test areas thereon. The test strip can also include a mobile phase membrane that is the same as, or different, from the stationary phase membrane.

In some aspects the labeled receptor comprises a labeled antibody, such as a polyclonal or monoclonal antibody. In other aspects the labeled receptor can be a labeled non-immunological receptor such as an enzyme. The labeled receptor can also be a combination of different receptors with differing affinities, such as differing affinities to the same analyte or affinity to different analytes. The label of the labeled receptor can be a colored particle, such as a gold particle.

Aspects include extraction and/or detection of one or more analytes including one or more toxins, such as mycotoxins, for example, aflatoxin, vomitoxin (DON), fumonisin, T2, zearlanone, patulin and ochratoxin from a variety of solid matrices including feeds and grains such as barley, corn, corn flour, corn meal, corn gluten meal, corn germ meal, wheat, soybeans, dried distillers grain (DDGS), distiller's corn meal, corn germ meal, corn/soy blend, cracked corn, hominy, oats, popcorn, rice, defatted rice bran, rough rice and milled rice, sorghum, and other similar matrices.

Aspects include providing an extraction composition that is compatible with a lateral flow test strip and can effectively and efficiently extract any of one or more of a variety mycotoxins from a variety of sample matrices. Such aspects include providing a standard extractant composition that can be used, with little or no alteration or adjustment, across a variety of matrices, analytes and/or tests.

Aspects include a composition that can both extract an analyte of interest and efficiently and effectively flow on a lateral flow test strip. Such aspects can include a composition that can both block binding sites on a chromatographic test strip membrane such as a nitrocellulose membrane and/or a POREX membrane and extract an analyte of interest. Such compositions can include, for example, bovine serum albumin (BSA) and/or polyethylene glycol (PEG). PEG based compositions can also be usefully combined with other materials such as other buffers, for example, POPSO (Piperazine-1,4-bis(2-hydroxy-3-propanesulfonic acid).

Aspects include providing an extraction composition that can be used to extract any of a number of toxins, such as mycotoxins, from any of a number of matrices, such as feed and grains, with little or no dilution or buffering prior to addition to a lateral flow test strip. Such aspects can include an extraction composition that also serves as an agent to block binding sites on a lateral flow test strip membrane, for example nitrocellulose.

Aspects include providing an extraction composition that can be used to extract any of a number of toxins, such as mycotoxins, from any of a number of matrices, such as feed and grains, with little or no dilution or buffering prior to addition to a lateral flow test strip. Such aspects can include an extraction composition that also serves as an agent to block binding sites on a lateral flow test strip membrane, for example nitrocellulose.

Aspects include providing an extraction composition that can be used extract one or more toxins from a sample for testing to detect one or more toxins in a single test such as a single lateral flow test strip.

Aspects include supplying the extraction composition, such as BSA, in dried form for mixing directly with the dry sample. Solvent, such as water, is added to the dry mixture and the mixture shaken before allowing the solid material to settle and testing the extract by sampling from the liquid layer above the solid layer. Alternatively, the extraction composition, such as BSA, can be dissolved in water prior to adding the dry sample. The dry sample can also be first mixed with solvent, such as water, and then combined with the dry extraction composition.

DETAILED DESCRIPTION

Provided are compositions and methods for facilitating the extraction of small molecules, such as mycotoxins, from agricultural products such as a variety of grains, corns and feeds. Although not wishing to be constrained by theory, useful extraction compositions have been found to be a variety of materials with relatively high ionic strength, such as a variety of proteins, amino acids and polyethylene glycol. Many of the herein described compositions and methods include the use of materials with high ionic strength such as materials having one or multiple amine groups including a variety of protein and amino acid based compositions and materials. Useful compositions can include one or more proteins and/or amino acids. A variety of proteins can be usefully employed including alone or in combination bovine collagen, bovine serum albumin (BSA), gelatin peptone, soy peptone, soy/casein Primatone® and Primatone® RL. BSA can be particularly useful since it is relatively inexpensive, readily available and compatible with many lateral flow test strips. For example, BSA is useful to block binding sites on nitrocellulose when nitrocellulose is a component of a test strip. In addition, BSA can be useful to enhance the flow along a test strip. When milk is the matrix, the casein in the milk can block binding sites on nitrocellulose and, therefore, the importance of utilizing other blocking agents may be reduced. When milk, or other matrices that include agents that block binding sites on chromatographic membranes, are not tested, the sites may need to be blocked and, therefore, BSA can be useful. The properties of BSA allow a BSA based solution to be used on a test strip with little or no further dilution. For that reason, when BSA is used as an extracting agent, higher sensitivity to analyte may be achievable.

Proteins, such as BSA, can be used in a mixture, for example including a salt such as a phosphate salt, citrate salt and/or chloride salt. Other possibly useful ingredients include certain wetting agents, chelators and preservatives.

An extraction can take place using a variety of methods including combining the sample with the extraction composition, shaking the sample in a container, mixing the sample with a stirrer, or mixing the sample with a blender. Depending on the composition, an antifoaming agent may be useful. Other possible extraction include filtering to collect the extract, allowing sample to sit to form an extract layer above the ground sample, or centrifuging a portion of the sample to obtain an extract layer and sample layer such as in cases in which an improved extract layer and sample layer is need, for example, if shaking and allowing to stand does not produce the desired separation.

The above described extraction methods can be useful to extract an analyte for detection in for a variety of detection methods and have been found particularly useful for extraction of one or more small molecules, such as one or more mycotoxins, in preparation for detection in lateral flow test strips. For lateral flow test strips, the sample extract can be tested directly or can be mixed with a dilution buffer. The dilution buffer can be used to allow a mobile phase to flow uniformly over the test strip. A mobile phase allows reconstitution of the dried reagents on the test strip. The extract can be diluted by a number of methods and a variety of possible dilution ratios of the extract with the dilution buffer. The dilution buffer can consist of, for example, phosphate buffer, or water. When the analyte is in sample liquid, such as fluid milk, the sample may not require dilution or extraction. When the sample is a solid, or semi-solid, and, therefore, must be combined with a liquid for test operation, the use of a composition for extraction, such as BSA and/or PEG based compositions, which can be added directly to a test strip without further dilution, is useful. Combinations with other materials, however, may nevertheless be desirable such as to alter the test sensitivity range or to allow consistency between samples.

It might also be desirable to, for example, extract the sample and then add the extract to a buffer prior to addition to a test strip. Although it might be possible to employ one step, in which the sample is extracted with BSA and the extract added to the test strip, extra BSA may be required to properly dilute the sample for effective test strip function. By minimizing the amount of BSA, and using the BSA only in an amount required to extract the analyte, test cost can be lowered. After extraction using the minimal amount of BSA required, the extract can be diluted with less costly (compared to BSA) dilution buffer prior to adding to the test strip.

Somewhat similarly, water soluble analytes, such as DON, may be extracted from samples using a composition that is partially or completely water. When testing for such analytes, however, it may still be useful to mix with a composition, such as a 5% BSA composition, prior to addition to a chromatographic test strip to block binding sites such as nitrocellulose binding sites, which might otherwise interfere with the operation.

Embodiments include using an extraction composition, such as BSA, in dried form and mixing the dried extraction composition directly with the dry sample. Solvent, such as water, can be added to the dry mixture and the mixture shaken before allowing the solid material to settle and testing the extract by sampling from the liquid layer above the solid layer. Alternatively, the extraction composition, such as BSA, can be dissolved in water prior to adding the dry sample. The dry sample can also be first mixed with solvent, such as water, and then combined with the dry extraction composition.

The lateral flow assay test strip can include a support strip and a sample-absorbing matrix. The test device also can include a mobile-phase support attached to the support strip and in contact with the sample-absorbing matrix. In an example, a mobile-phase composition is disposed within or on the test device and has one or more labeled receptors, such as one or more gold labeled antibodies.

The mobile-phase composition can be applied prior to test operation, for example by spraying and drying onto a porous surface such as a polyethylene membrane. When exposed to a sample, the mobile-phase composition can be carried in the sample flow together with the sample. In test operation, the sample flows and, when a receptor is an antibody, the antibody binds to an analyte present in the sample to form an antibody-analyte complex. Alternatively, the mobile phase can be combined with sample prior to application to the test strip or other solid support. In this alternative embodiment, antibody can bind to analyte in the sample prior to contact with the test strip.

In an example, the test strip includes a stationary-phase support strip, which may be part of the same strip as the mobile-phase composition support strip, or on a separate strip in fluid flow contact with the first strip. A support strip can have a first membrane end in contact with the mobile-phase composition and a second membrane end that may be in contact with an optional disposal zone. Lateral-capillary flow of the sample is from the first membrane end to the second membrane end. The test strip can also be wholly or partially of a material, for example nitrocellulose, that can bind proteins. A variety of materials can be used in various portions of the strip including natural or synthetic materials including cellulosic materials such as paper, cellulose and cellulose derivatives such as cellulose acetate and nitrocellulose; fiberglass; glass fiber filter, for example WHATMAN® Fusion 5 membrane (Whatman® is a registered trademark of Whatman Paper Limited, Kent, England); cloth, both naturally occurring and synthetic; porous gels such as silica gel, agarose, dextran and gelatin; porous fibrous matrices; starch based materials, such as cross-linked dextran chains; ceramic materials; films of polyvinyl chloride and combinations of polyvinyl chloride-silica; POREX® (Porex® is a registered trademark of Porex Technologies Corp., Fairburn, Ga.) and the like. Generally, the material used in the flow stream should allow liquid to flow on or through the strip. If a variety of materials are used they can be in fluid flow communication/contact or capable of being brought into fluid flow communication/contact. The strip should have sufficient inherent strength or additional strength can be provided by a supplemental support such as a plastic backing upon which porous or bibulous strip components are attached.

One or more test zones can be located on the test strip and may include a capture agent, such as a representative analyte or analogue thereof, which captures unbound labeled receptor, such as unbound labeled antibody. Examples of possible test zone capture agents include aflatoxin, or other toxins such as ochratoxin, DON, T2, patulin, zearlanone and fumonisin, depending on the analyte to be detected. Such a capture agent may be disposed on the test zone portion of the membrane for example by spraying. Prior to spraying, said capture agent can be conjugated to an attachment or carrier protein. Suitable attachment proteins are known to those skilled in the art to be proteins that bind readily to solid supports, such supports that include nitrocellulose. A useful attachment protein includes a carrier protein, i.e., a protein commonly used in conjunction with an immunogen, such as generally water soluble proteins with multiple accessible amino groups including albumin, e.g., bovine serum albumin (BSA), ovalbumin (OVA), keyhole limpet hemocyanin (KLH) and thyroglobulin (THG).

One or more optional control zones may also be on the test strip. The control zone may contain capture agent for the analyte receptor, such as an antibody with affinity to the analyte. Such capture agent can include antibody to the particular antibody, such as anti-species antibody, for binding with both analyte-bound antibody and excess unbound antibody. Alternatively, the control zone may be involved in an independent reaction that informs the user that the test is complete and includes consistent visual indicators, such as color development, for comparison to the test zone. The control zone can generate signal either on contact with sample or on contact with specific test material, such as labeled antibody, such as when the control zone includes an anti-species antibody or one of the several useful antibody capture agents known in the art including protein A, protein G or recombinant varieties of proteins A and G.

The lateral flow test device and method can also be in a sandwich assay format or, as described above, an inhibition/competitive format.

Lateral flow test results can be interpreted visually or by use of a reader, or analyzer, such as a ROSA® reader (ROSA® is a registered trademark of Charm Sciences, Inc. Lawrence, Mass.), or Charm EZ® reader (Charm EZ® is a registered trademark of Charm Sciences, Inc. Lawrence, Mass.). Other reader/analyzer examples include fluorometers, luminometers, bar code readers, radiation detectors (such as scintillation counters), UV detectors, infrared detectors, electrochemical detectors or optical readers, such as spectrophotometers. The reader can be used to distinguish between one or more test zones and one or more control zones or simply to determine a relative change in the test zone. In one embodiment the reader is a ROSA reader. In a particular embodiment, the analyzer is an optical reader, e.g., the reader described in U.S. Pat. No. 6,124,585, issued Sep. 26, 2000, hereby incorporated by reference. In a quantitative test, the changes in the test areas, and, when a control zone is present, the extent of the difference between the control zone and test zone or test areas (test area and test zone are used interchangeably herein), can determine the test range detection level of analyte. To accurately and/or numerically assess the differences and the binding at the control zone and test zone, particularly in a quantitative assay, a reader is useful. The reader can also include, within its settings, various selectable calibration settings. Such calibration settings can be editable or changeable depending on the matrix being tested and/or the analyte being detected. In that way, for example, a standard curve can be adjusted to reflect the efficiency of extraction of a particular analyte from a particular matrix. Such an adjustable reader can be particularly useful to allow standardization of a surfactant based extraction solution, such as described herein, for use with a variety of matrices and a variety of analytes. Reader settings can also be adjusted automatically by reading test strip elements, for example by using EZ Compatible® (EZ Compatible® is a registered trademark of Charm Sciences, Inc. Lawrence, Mass.) in conjunction with a Charm EZ® reader as described in PCT/US2011/049170, filed Aug. 25, 2011 ("Lateral Flow Assay Analysis") and PCT/US11/35576, Filed May 6, 2011 ("Device, System and Method for Transit Testing"), each of which is hereby incorporated by reference.

In a particular embodiment, the mobile phase contacts, or is put into contact with, a first test area on a solid support. The solid support can be configured to allow the mobile phase to flow from the first test area to a second test area on the solid support and, if a control zone is included, to the control zone. The first test area can include a capture agent immobilized on the solid support. The first test area capture agent will have greater binding affinity to the receptor than to the receptor-analyte complex. As a result of that differential in binding affinity, captured receptor in the test area will decrease as sample analyte concentration increases. When there is a second test area, the second test area can also include a capture agent immobilized on the solid support. As with the first area capture agent, the second test area capture agent will have greater binding affinity to the receptor than to the receptor-analyte complex. The capture agent can be the same in each of the test areas and at the same or different concentrations in each area. The capture agents can also be different, for example with different binding characteristics to the receptor. The capture agents in different test areas can also be targeted to entirely separate receptors, such as when the test strip is designed to detect multiple analytes.

The receptor can be labeled with a label, such as a colored particle, that can be detected when the receptor is bound to the solid support via capture by the capture agent immobilized on the solid support. The intensity of the detectable signal, for example a visible signal, at the first and second test areas can be measured to determine a result. In an inhibition style test the strength (intensity) of the signals are inversely related to the concentration of analyte in the sample. The signal intensities can be observed visually or measured by an electronic test instrument. For example the intensity at each of the two test areas can be summed to determine a result that can relate to the concentration of an analyte in the sample.

Various suitable labels include chromogens, catalysts, fluorescent compounds, chemiluminescent compounds, radioactive labels, magnetic beads or magnetic particles, enzymes or substrates, vesicles containing signal producing substances, colorimetric labels, direct visual labels including colloidal metallic and metallic and non-metallic colored particles, dye particles, or organic polymer latex colored particles.

Additional embodiments for use in the methods set forth herein are set forth in U.S. patent application Ser. No. 12/080,044, filed Mar. 31, 2008 (hereby incorporated by reference).

Presence or absence tests, known in the art as qualitative tests, provide a yes or no result. Tests that detect the presence or absence of a target analyte above or below a certain threshold level are known as semi-quantitative tests. Tests that determine that a target analyte is present at a particular concentration, or within a range of concentrations, are known as quantitative tests.

Although, many of the herein examples and descriptions refer to detecting mycotoxins such as aflatoxin, zearalanone, patulin, DON, fumonisin and ochratoxin, other analytes can be detected and quantified in a variety of matrices using the herein disclosure. Other possible target analytes include hormones, vitamins, drugs, metabolites and their receptors and binding materials, antibodies, peptides, protein, allergens, fungicides, herbicides, pesticides and plant, animal and microbial toxins may be determined using the present methods and apparatuses. Other analytes that may be determinable by this disclosure include antibiotics, such as beta-lactams, cephalosporins, erythromycin, sulfonamides, tetracyclines, nitrofurans, quinolones, vancomycin, gentamicin, amikacin, chloramphenicol, streptomycin and tobramycin, toxins, and drugs of abuse, such as opioids and the like, as well as the metabolites of any of the above listed possible target analytes.

Although much of the description herein relates to use of the extraction compositions for extracting analytes for detection using lateral flow type devices and tests, it will be appreciated that the extraction compositions described herein may also be useful to extract analytes, such as toxins, prior to detection in other test formats, for example ELISA assays, radiobinding assays such as those available from Charm Sciences, Inc. (Lawrence, Mass.) and known as the Charm II assays, and other detection methods and tests.

Numerous embodiments and advantages of this disclosure have been set forth in the foregoing description. Many of the novel features are captured in the following claims. The disclosure, however, is illustrative only, and modifications by one of skill in the art may be made with the present disclosure without departing from the scope of the invention.

EXAMPLES

Within the tables, T1 is test line 1 result; T2 is test line 2 result; C is Control line result; RR Conc is the concentration provided by the ROSA Reader (using a preprogrammed algorithm); Result is Rosa Reader result. The ROSA Reader is programmed to provide a result and RR concentration. The result is calculated from a comparison of T1 and T2 with C using an algorithm. The "spread" is the difference between the result for a negative control (NC) result and the result with the particular analyte concentration. The RR Conc is determined by the ROSA Reader through a calculation that associates the Result with a concentration for the particular toxin and matrix. "ppb"="parts per billion".

Example 1: Previously Dissolved BSA (Extraction Composition) Mixed with Dry Sample In Tables 1-3 the ROSA reader was calibrated using results from extractions using 70% methanol and, therefore, RR Conc is relevant. For Tables 4-14, the RR Conc results are not calibrated and, therefore, serve only as a relative indicator of detection (the concentration is not accurate because the reader is not calibrated).

Table 1 results are from an experiment using a 70% methanol extraction solution. The original sample was 1000 ppb fumonisin B1, B2 and B3 in corn and the sample was diluted to an in-assay concentration of 10.6 ppb. % cross-reactivity is a ratio of the RR Conc for a cross-reacting analyte (in Tables 1-3 fumonisin B2 and B3) with the RR Conc for B1. A lower cross-reactivity percentage indicates greater specificity to the analyte of detection, which in Tables 1-3 is fumonisin B1. It can be desirable to have cross-reactivity, such as when detection of the cross-reacting substances is desired. Cross-reactivity is, however, undesirable when the cross-reacting substance is not to be detected and, therefore, is a test interference. Results are in parts per trillion. For example, the RR Conc result in Table 1, for in-assay 10.6 ppb B1 is an RR Conc for the sample of 0.933 ppm, or 933 ppb.

TABLE 1

| Conc | | T1 | T2 | C | RR Conc | Result |
|---|---|---|---|---|---|---|
| 10.6 ppb B1 | | 2710 | 4513 | 2445 | 0.9 | −2333 |
| | | 3107 | 3451 | 2223 | 1 | −2112 |
| | | 2672 | 4027 | 2176 | 0.9 | −2347 |
| | AVE | 2830 | 3997 | 2281 | 0.933 | −2264 |
| | % CV | 9% | 13% | 6% | 6% | 6% |
| 10.6 ppb B2 | | 4581 | 4951 | 2380 | 0.2 | −4772 |
| | | 4166 | 4196 | 2074 | 0.3 | −4214 |
| | | 3543 | 4505 | 2123 | 0.4 | −3802 |
| | AVE | 4097 | 4551 | 2192 | 0.300 | −4263 |
| | % CV | 13% | 8% | 7% | 33% | 11% |
| % Cross reactive, B1 = 100% | | | | | 32% | |
| 10.6 ppb B3 | | 3548 | 4735 | 2485 | 0.55 | −3313 |
| | | 3408 | 4734 | 2673 | 0.75 | −2796 |
| | | 3211 | 4834 | 2293 | 0.5 | −3459 |
| | AVE | 3389 | 4768 | 2484 | 0.600 | −3189 |
| | % CV | 5% | 1% | 8% | 22% | 11% |
| % Cross reactive, B1 = 100% | | | | | 64% | |

Table 2 results are from an experiment using a 5% BSA extraction solution. The original sample was 1000 ppb and the sample was diluted to an in-assay concentration of 22.7 ppb. Results show higher RR Conc as is appropriate given the higher concentration (22.7 ppb) and similar cross-reactivity.

TABLE 2

| Conc | | T1 | T2 | C | RR Conc | Result |
|---|---|---|---|---|---|---|
| 22.7 ppb B1 | | 1990 | 4016 | 2936 | 2.3 | −134 |
| | | 1924 | 3323 | 2641 | 2.5 | 35 |
| | | 1875 | 3379 | 2700 | 2.6 | 146 |

TABLE 2-continued

| Conc | | T1 | T2 | C | RR Conc | Result |
|---|---|---|---|---|---|---|
| | AVE | 1930 | 3573 | 2759 | 2.467 | 16 |
| | % CV | 3% | 11% | 6% | 6% | |
| 22.7 ppb B2 | | 2988 | 4282 | 2635 | 1 | −2000 |
| | | 2827 | 4077 | 2508 | 1.1 | −1888 |
| | | 2744 | 4482 | 2558 | 1 | −2110 |
| | AVE | 2853 | 4280 | 2567 | 1.033 | −1999 |
| | % CV | 4% | 5% | 2% | 6% | 6% |
| % Cross reactive, B1 = 100% | | | | | 42% | |
| 22.7 ppb B3 | | 2554 | 3893 | 2986 | 2 | −475 |
| | | 2757 | 3990 | 2846 | 1.6 | −1055 |
| | | 2279 | 3770 | 2581 | 1.7 | −887 |
| | AVE | 2530 | 3884 | 2804 | 1.767 | −806 |
| | % CV | 9% | 3% | 7% | 12% | 37% |
| % Cross reactive, B1 = 100% | | | | | 72% | |

Table 3 results are from an experiment using a 5% BSA extraction solution. The original sample was 1000 ppb and the sample was diluted to an in-assay concentration of 10.6 ppb. Results show similar detection levels as with the methanol extraction at 10.6 ppb and similar cross-reactivity.

TABLE 3

| Conc | | T1 | T2 | C | RR Conc | Result |
|---|---|---|---|---|---|---|
| 10.6 ppb B1 | | 3018 | 5064 | 2961 | 1 | −2160 |
| | | 2847 | 3393 | 2071 | 1 | −2098 |
| | | 3375 | 3562 | 2404 | 1 | −2129 |
| | AVE | 3080 | 4006 | 2479 | 1.000 | −2129 |
| | % CV | 9% | 23% | 18% | 0% | 1% |
| 10.6 ppb B2 | | 3242 | 4743 | 2194 | 0.45 | −3597 |
| | | 3361 | 4650 | 1832 | 0.3 | −4347 |
| | | 3286 | 4588 | 2085 | 0.45 | −3704 |
| | AVE | 3296 | 4660 | 2037 | 0.400 | −3883 |
| | % CV | 2% | 2% | 9% | 22% | 10% |
| % Cross reactive, B1 = 100% | | | | | 40% | |
| 10.6 ppb B3 | | 2921 | 4029 | 2339 | 0.95 | −2272 |
| | | 3123 | 4379 | 2364 | 0.75 | −2774 |
| | | 3251 | 4678 | 2234 | 0.5 | −3461 |
| | AVE | 3098 | 4362 | 2312 | 0.733 | −2836 |
| | % CV | 5% | 7% | 3% | 31% | 21% |
| % Cross reactive, B1 = 100% | | | | | 73% | |

Tables 4-14 include results from tests using a variety of extraction compositions that include a variety of protein and amino acid based extraction solutions as indicated within each table. All protein solutions were five percent (5%) protein in 20 mM NaPO4 at pH 7.2. Amino acid and other solution are 0.2M. NC results are for a negative control. ND results are for samples with zero detected aflatoxin in a sample by a reference method (depending on the limit of detection of the reference method it is possible some aflatoxin is present in ND samples). The data in table 4 shows a "spread" of 6391 between the NC result (in some cases, as in table 4, the average of two NC results) and result with a sample originally spiked at 90 ppb aflatoxin which was diluted to an in-assay concentration of approximately 5.2 ppb (90/4/4.3).

TABLE 4

5% Primatone RL

| NC | T1 | T2 | C | Result |
|---|---|---|---|---|
|  | 3934 | 4154 | 2318 | −3452 |
|  | 3698 | 4078 | 2022 | −3732 |
| AVE | 3816 | 4116 | 2170 | −3592 |
| ND | 3733 | 4049 | 2005 | −3772 |
| 5.2 ppb | 1078 | 2397 | 3137 | 2799 |
| Spread |  |  |  | 6391 |

TABLE 5

5% Bovine collagen

|  | T1 | T2 | C | Result |
|---|---|---|---|---|
| NC | 4614 | 4526 | 2357 | −4426 |
|  | 4194 | 4430 | 2325 | −3974 |
| AVE | 4404 | 4478 | 2341 | −4200 |
| ND | 4436 | 4709 | 2401 | −4343 |
| 5.2 ppb | 738 | 2163 | 3936 | 4971 |
| Spread |  |  |  | 9171 |

TABLE 6

85% Casein, 15% soy

|  | T1 | T2 | C | Result |
|---|---|---|---|---|
| NC | 3847 | 4399 | 2571 | −3104 |
| ND | 3575 | 3809 | 1917 | −4343 |
| 5.2 ppb | 957 | 2471 | 3503 | 3578 |
| Spread |  |  |  | 6682 |

TABLE 7

5% Gelatin Peptone

|  | T1 | T2 | C | Result |
|---|---|---|---|---|
| NC | 4494 | 4555 | 2072 | −4905 |
| ND | 4066 | 3990 | 2011 | −4034 |
| 5.2 ppb | 1400 | 2947 | 3815 | 3283 |
| Spread |  |  |  | 8188 |

TABLE 8

5% Soy Peptone

|  | T1 | T2 | C | Result |
|---|---|---|---|---|
| NC | 4419 | 4159 | 2176 | −4226 |
| ND | 4263 | 4224 | 2171 | −4145 |
| 5.2 ppb | 1176 | 2460 | 3183 | 2730 |
| Spread |  |  |  | 6956 |

TABLE 9

0.2M Glycine pH 7.2

|  | T1 | T2 | C | Result |
|---|---|---|---|---|
| NC | 4337 | 4510 | 2059 | −4729 |
| ND | 3820 | 4151 | 2232 | −3507 |
| 5.2 ppb | 1234 | 2566 | 3157 | 2514 |
| Spread |  |  |  | 7243 |

TABLE 10

0.2M Arginine pH 7.2

|  | T1 | T2 | C | Result |
|---|---|---|---|---|
| NC | 4088 | 4155 | 1799 | −4645 |
| ND | 3901 | 4115 | 1812 | −4392 |
| 5.2 ppb | 664 | 1945 | 3091 | 3573 |
| Spread |  |  |  | 8218 |

TABLE 11

0.2M Diaminopropane pH 7.2

|  | T1 | T2 | C | Result |
|---|---|---|---|---|
| NC | 3707 | 4062 | 2239 | −3291 |
| ND | 3791 | 4043 | 2311 | −3212 |
| 5.2 ppb | 1014 | 2488 | 3272 | 3042 |
| Spread |  |  |  | 6333 |

TABLE 12

0.2M Na Phos pH 7.2

|  | T1 | T2 | C | Result |
|---|---|---|---|---|
| NC | 4294 | 4218 | 2205 | −4102 |
| ND | 4121 | 4077 | 2306 | −3586 |
| 5.2 ppb | 1727 | 3038 | 3838 | 2911 |
| 5.2 ppb | 1590 | 2784 | 3390 | 2406 |
| AVE | 1659 | 2911 | 3614 | 2659 |
| Spread |  |  |  | 6761 |

TABLE 13

0.02M NA PO4 pH 7.2

|  | T1 | T2 | C | Result |
|---|---|---|---|---|
| NC | 3072 | 3551 | 1801 | −3021 |
| 5.2 ppb | 1579 | 2648 | 3109 | 1991 |
| Spread |  |  |  | 5012 |

TABLE 14

0.02M Arginine pH 7.2

|  | T1 | T2 | C | Result |
|---|---|---|---|---|
| NC | 3883 | 4136 | 1960 | −4099 |
| ND | 3994 | 4210 | 2029 | −4146 |
| 5.2 ppb | 1401 | 2689 | 3143 | 2196 |
| Spread |  |  |  | 6295 |

Tables 15 and 16 include results from tests using a BSA based extraction composition. The composition included 5% protein (BSA) in 0.1M Na PO4 at pH 7.4 and 0.08% KATHON® (Rohm And Haas Company, Philadelphia Pa.). Table 15 in-assay concentrations of aflatoxin in the sample are at 0, 2.16, 5.6, 11, 19.5, 90.1 parts per billion (PPB) (concentrations shown on far left of table). As can be seen, the difference between the result at 0 ppb and the various concentrations (the spread) grows as the concentration of aflatoxin in the sample is increased. Table 16 results are from a test sample that was diluted 4.3 fold. As a result, the in-assay concentrations are effectively decreased by 4.3 from the concentration shown on the left of the table (for example 90.1 is actually an in-test concentration of 20.95 (90.1/4.3).

TABLE 15

1x

| Conc | | T1 | T2 | C | RR Conc | Result |
|---|---|---|---|---|---|---|
| 0 | | 3886 | 3773 | 2359 | 0 | −2941 |
| | | 3785 | 3082 | 1844 | 0 | −3179 |
| | | 3421 | 3323 | 2002 | 1 | −2740 |
| | | 3862 | 3919 | 2431 | 0 | −2919 |
| | AVE | 3739 | 3524 | 2159 | 0 | −2945 |
| | % CV | 6% | 11% | 13% | 200% | 6% |
| 2.16 | | 2688 | 2714 | 2542 | 7 | −318 |
| | | 2920 | 2589 | 2365 | 5 | −779 |
| | | 3266 | 2825 | 2715 | 5 | −661 |
| | | 3254 | 3204 | 2944 | 6 | −570 |
| | AVE | 3032 | 2833 | 2642 | 6 | −582 |
| | % CV | 9% | 9% | 9% | 17% | 34% |
| 5.6 | | 1984 | 2408 | 2847 | 19 | 1302 |
| | | 2124 | 2297 | 2730 | 16 | 1039 |
| | | 2232 | 2703 | 2989 | 16 | 1043 |
| | | 2357 | 2540 | 3150 | 20 | 1403 |
| | AVE | 2174 | 2487 | 2929 | 18 | 1197 |
| | % CV | 7% | 7% | 6% | 12% | 15% |
| 11 | | 915 | 1642 | 2750 | 50 | 2943 |
| | | 1459 | 1956 | 2945 | 30 | 2475 |
| | | 1329 | 2144 | 3065 | 42 | 2657 |
| | | 993 | 1662 | 2827 | 52 | 2999 |
| | AVE | 1174 | 1851 | 2897 | 44 | 2769 |
| | % CV | 22% | 13% | 5% | 23% | 9% |
| 19.5 | | 972 | 1644 | 3038 | 67 | 3460 |
| | | 1007 | 1752 | 3055 | 63 | 3351 |
| | | 755 | 1438 | 2505 | 47 | 2817 |
| | | 799 | 1440 | 2775 | 62 | 3311 |
| | AVE | 883 | 1569 | 2843 | 60 | 3235 |
| | % CV | 14% | 10% | 9% | 15% | 9% |
| 90.1 | | 289 | 950 | 3643 | 150 | 6047 |
| | | 251 | 964 | 3633 | 150 | 6051 |
| | | 88 | 734 | 3145 | 150 | 5468 |
| | | 136 | 908 | 3678 | 150 | 6312 |
| | AVE | 191 | 889 | 3525 | 150 | 5970 |
| | % CV | 50% | 12% | 7% | 0% | 6% |

TABLE 16

4.3x

| Conc | | T1 | T2 | C | RR Conc | Result |
|---|---|---|---|---|---|---|
| 0 | | 3778 | 4268 | 1923 | 0 | −4200 |
| | | 4050 | 4229 | 2122 | 0 | −4035 |
| | | 3858 | 3715 | 1923 | 0 | −3727 |
| | | 4002 | 4287 | 2302 | 0 | −3685 |
| | AVE | 3922 | 4125 | 2068 | 0 | −3912 |
| | % CV | 3% | 7% | 9% | 0% | 6% |
| 2.16 | | 4094 | 4378 | 2494 | 0 | −3484 |
| | | 4139 | 4679 | 2726 | 0 | −3366 |
| | | 4128 | 4498 | 2637 | 0 | −3352 |
| | | 3524 | 4132 | 2357 | 0 | −2942 |
| | AVE | 3971 | 4422 | 2554 | 0 | −3286 |
| | % CV | 8% | 5% | 6% | 0% | 7% |
| 5.6 | | 3745 | 4267 | 2665 | 1 | −2682 |
| | | 3819 | 3614 | 2338 | 1 | −2757 |
| | | 4005 | 4250 | 2723 | 1 | −2809 |
| | | 3809 | 4268 | 2641 | 1 | −2795 |
| | AVE | 3845 | 4100 | 2592 | 1 | −2761 |
| | % CV | 3% | 8% | 7% | 0% | 2% |
| 11 | 5 | 2743 | 3114 | 2495 | 5 | −867 |
| | 5 | 2811 | 3647 | 2691 | 4 | −1076 |
| | 5 | 3664 | 4027 | 3018 | 2 | −1655 |
| | 5 | 3157 | 3573 | 2895 | 4 | −940 |
| | AVE | 3094 | 3590 | 2775 | 4 | −1135 |
| | % CV | 14% | 10% | 8% | 34% | 32% |

TABLE 16-continued 4.3x

| Conc | | T1 | T2 | C | RR Conc | Result |
|---|---|---|---|---|---|---|
| 19.5 | 5 | 2715 | 3672 | 3572 | 14 | 757 |
| | 5 | 2837 | 3810 | 3540 | 11 | 433 |
| | 5 | 2475 | 3281 | 3312 | 15 | 868 |
| | 5 | 2080 | 3053 | 3015 | 15 | 897 |
| | AVE | 2527 | 3454 | 3360 | 14 | 739 |
| | % CV | 13% | 10% | 8% | 14% | 29% |
| 90.1 | 5 | 700 | 1736 | 3815 | 150 | 5194 |
| | 5 | 616 | 1539 | 3342 | 124 | 4529 |
| | 5 | 832 | 1967 | 3977 | 150 | 5155 |
| | 5 | 684 | 1824 | 3708 | 150 | 4908 |
| | AVE | 708 | 1767 | 3711 | 144 | 4947 |
| | % CV | 13% | 10% | 7% | 9% | 6% |

Example 2: Dry BSA (Extraction Composition) Mixed with Dry Sample and the Combination Mixed with Water (Evaluation of Charm ROSA WET Aflatoxin Quantitative Test for Feed and Grain (AFQ-WET)

50 grams corn was combined with dry BSA extraction composition and the combination mixed with 150 mL water (amount of water 3× weight of extraction composition). The mixture was shaken vigorously for 1-2 minutes and then allowed to settle for 1 minute to obtain sample extract. Sample tested was from liquid extract layer above settled solid layer.

First quantitation range: 0-20 ppb aflatoxin.

0.300 mL sample extract was added to 0.300 mL AFQ-B dilution buffer (3.5% BSA in 0.1M $NaPO_4$ (AFQ-B dilution buffer is a product of Charm Sciences, Lawrence, Mass.) and mixed.

Second quantitation range: 20-100 ppb.

0.300 mL extract was added to 1.0 mL AFQ-B dilution buffer and mixed.

Aflatoxin-corn assay was run at 5.61 ppb, 11 ppb, 20.6 ppb (run twice, once with results compared to a dose-response curve set for the 0-20 ppb curve and second time, after dilution in buffer, with reference to a 20-100 ppb dose response curve.) 21 test strips were run at each concentration including zero control and positive control 20 ppb). All 21 strips were 0 for negative control and positive at 20 ppb with positive control (result range 14-25 ppb with mean of 18 ppb, standard deviation of 3 and % CV of 16.7%. 0 was result for 0 20/21 strips with one strip registering 1. At 5.61 ppb the result range was 5-8 ppb with a mean of 6.2 ppb, a standard deviation of 0.9. At 11 ppb the result range was 9-12 with a mean of 11 ppb a standard deviation of 1 and % CV of 9.1%. At 20.6 ppb the result range was 18-27 ppb, the mean was 22 ppb, the standard deviation was 2 and % CV was 9.1%.

The 20.6 ppb result range, on the 100 ppb dose response curve (sample diluted additional 4.3× from above), was 10-27. The one 10 ppb result was out of range. The mean was 19 ppb, the standard deviation was 4 ppb and the % CV was 21.1%. The 93.2 ppb sample result range was 70-102 with a mean of 84, a standard deviation of 8 and % CV of 9.5%.

1. Time required for completion of an analysis:
   The test kit is capable of analyzing a single sample in less than 30 minutes with a pre-ground sample.

| Extraction and Sample Preparation: | 4 minutes |
|---|---|
| AFQ-WET Test Procedure: | 5 minutes |
| Reader Interpretation: | 0.5 minutes |
| Total Time: | 9.5 minutes |

2. Comparative accuracy of test kits on corn samples naturally contaminated with Aflatoxin. Comparative accuracy of test kit was conducted on naturally contaminated corn. Samples were ground using a Bunn G3 grinder and passed through a 20-mesh sieve. Material that did not pass through the 20-mesh sieve were ground using a Perten LabMill 3100 with a 20-mesh sieve, at which time both portions were combined and mixed on an inversion mixer for at least 24 hours. Sample aliquots of 50 g were obtained throughout the entire sample at each concentration. HPLC analysis was conducted on 21 samples over a 3 day period. AFQ-WET analysis was conducted by 3 operators each testing 7 samples on a unique lot of test strips according to the operator's manual.

TABLE 17

HPLC Analysis of Corn

|  |  | 5 ppb | 10 ppb | 20 ppb | 100 ppb |
|---|---|---|---|---|---|
| Day 1 | 1 | 4.90 | 9.92 | 22.2 | 90.0 |
|  | 2 | 5.88 | 11.1 | 17.9 | 90.1 |
|  | 3 | 7.00 | 11.0 | 24.8 | 90.7 |
|  | 4 | 5.40 | 11.85 | 21.7 | 88.2 |
|  | 5 | 7.38 | 10.0 | 18.4 | 107.2 |
|  | 6 | 5.38 | 11.0 | 21.5 | 97.0 |
|  | 7 | 5.66 | 10.2 | 19.9 | 95.8 |
| Day 2 | 1 | 5.07 | 10.9 | 19.6 | 97.3 |
|  | 2 | 6.01 | 10.45 | 22.3 | 83.2 |
|  | 3 | 5.60 | 10.88 | 22.8 | 117.5 |
|  | 4 | 5.23 | 10.7 | 22.7 | 88.1 |
|  | 5 | 5.44 | 14.02 | 19.9 | 86.1 |
|  | 6 | 5.65 | 10.4 | 21.5 | 96.1 |
|  | 7 | 5.64 | 11.1 | 21.6 | 100.4 |
| Day 3 | 1 | 5.52 | 11.77 | 19.8 | 86.6 |
|  | 2 | 5.07 | 10.29 | 19.9 | 100.9 |
|  | 3 | 4.93 | 10.9 | 19.3 | 92.2 |
|  | 4 | 6.13 | 12.87 | 18.7 | 87.2 |
|  | 5 | 5.32 | 10.28 | 18.8 | 82.3 |
|  | 6 | 5.33 | 10.77 | 19.1 | 93.2 |
|  | 7 | 5.32 | 10.4 | 19.4 | 86.3 |
|  | Average | 5.61 | 11.0 | 20.6 | 93.2 |
|  | Std Dev | 0.62 | 1.0 | 1.8 | 8.4 |
|  | % CV | 11% | 9% | 9% | 9% |

TABLE 18

AFQ-WET Analysis of Corn

|  |  | MATRIX | 5 ppb 00 | 10 ppb 00 | 20 ppb 00 | 100 ppb 01 |
|---|---|---|---|---|---|---|
| Analyst 1 | 1 |  | 4 | 9 | 19 | 99 |
| Lot 001A | 2 |  | 5 | 9 | 19 | 96 |
|  | 3 |  | 6 | 12 | 22 | 85 |
|  | 4 |  | 5 | 9 | 23 | 90 |
|  | 5 |  | 4 | 9 | 20 | 81 |
|  | 6 |  | 5 | 10 | 15 | 98 |
|  | 7 |  | 3 | 9 | 18 | 107 |
| Analyst 2 | 1 |  | 5 | 11 | 18 | 84 |
| Lot 001B | 2 |  | 5 | 13 | 20 | 86 |
|  | 3 |  | 7 | 14 | 18 | 81 |
|  | 4 |  | 6 | 11 | 22 | 74 |
|  | 5 |  | 6 | 11 | 18 | 78 |
|  | 6 |  | 6 | 11 | 22 | 88 |
|  | 7 |  | 5 | 12 | 20 | 110 |

TABLE 18-continued

AFQ-WET Analysis of Corn

| Analyst 3 | 1 | 5 | 13 | 23 | 109 |
|---|---|---|---|---|---|
| Lot 001C | 2 | 6 | 12 | 22 | 81 |
|  | 3 | 6 | 12 | 20 | 93 |
|  | 4 | 6 | 11 | 21 | 96 |
|  | 5 | 6 | 12 | 21 | 80 |
|  | 6 | 7 | 13 | 22 | 97 |
|  | 7 | 7 | 11 | 21 | 120 |
|  | Average | 5.48 | 11.1 | 20.2 | 92.0 |
|  | Std Dev | 1.03 | 1.5 | 2.0 | 12.2 |
|  | % CV | 19% | 14% | 10% | 13% |

Acceptable Ranges:

| ppb | Lower | To | Upper |
|---|---|---|---|
| 5.61 | 2.81 | to | 8.42 |
| 11.0 | 6.2 | to | 15.8 |
| 20.6 | 12.3 | to | 28.8 |
| 93.2 | 63.4 | to | 123.0 |

Example 3: Suggested Additional Commodities

Additional commodity testing was conducted on non-detect samples, according to the methods used in Example 2. Samples were ground using a Bunn G3 grinder (Bunn-O-Matic Corporation, Springfield, Ill.) and passed through a 20-mesh sieve. Material that did not pass through the 20-mesh sieve were ground using a Perten LabMill (Perten Instruments®, Hägersten, Sweden) and passed through a 20-mesh sieve, at which time both portions were combined and mixed on a Turbula® mixer (Willy A. Bachofen Ag, Muttenz, Switzerland) for 4 hours. Sample aliquots of 50 g were obtained throughout the entire sample and fortified with an aflatoxin reference standard to prepare 5 and 20 ppb samples AFQ-WET analysis was conducted by one operator testing 5 samples at each concentration. Validations were completed for the following additional commodities passing all specifications:

Table Set 19:

|  | Barley | | | Corn Flour | | |
|---|---|---|---|---|---|---|
|  | ND | 5 ppb | 20 ppb | ND | 5 ppb | 20 ppb |
|  | 0 | 7 | 23 | 0 | 3 | 22 |
|  | 0 | 6 | 22 | 0 | 3 | 25 |
|  | 0 | 7 | 24 | 0 | 4 | 22 |
|  | 0 | 7 | 25 | 0 | 5 | 23 |
|  | 0 | 5 | 23 | 0 | 3 | 22 |
| Average | 0 | 6 | 23 | 0 | 4 | 23 |
| Std dev | 0 | 1 | 1 | 0 | 1 | 1 |
| % CV | NA | 14% | 5% | NA | 25% | 6% |

|  | Corn Germ Meal | | | Corn Meal | | |
|---|---|---|---|---|---|---|
|  | ND | 5 ppb | 20 ppb | ND | 5 ppb | 20 ppb |
|  | 0 | 4 | 17 | 0 | 5 | 19 |
|  | 0 | 3 | 19 | 0 | 6 | 21 |
|  | 0 | 4 | 17 | 0 | 5 | 16 |
|  | 1 | 3 | 14 | 0 | 4 | 22 |
|  | 1 | 3 | 18 | 0 | 6 | 21 |
| Average | 0 | 3 | 17 | 0 | 5 | 20 |
| Std dev | 1 | 1 | 2 | 0 | 1 | 2 |
| % CV | 137% | 16% | 11% | NA | 16% | 12% |

|  | Corn/Soy Blend | | | DDGS | | |
|---|---|---|---|---|---|---|
|  | ND | 5 ppb | 20 ppb | ND | 5 ppb | 20 ppb |

Table Set 19:

|  | 1 | 5 | 17 | 1 | 4 | 16 |
|---|---|---|---|---|---|---|
|  | 0 | 6 | 17 | 1 | 4 | 17 |
|  | 0 | 6 | 19 | 1 | 5 | 18 |
|  | 0 | 5 | 19 | 0 | 5 | 17 |
|  | 1 | 5 | 18 | 1 | 5 | 18 |
| Average | 0 | 5 | 18 | 1 | 5 | 17 |
| Std dev | 1 | 1 | 1 | 0 | 1 | 1 |
| % CV | 137% | 10% | 6% | 56% | 12% | 5% |

|  | Hominy | | | Oats | | |
|---|---|---|---|---|---|---|
|  | ND | 5 ppb | 20 ppb | ND | 5 ppb | 20 ppb |
|  | 0 | 3 | 17 | 0 | 4 | 14 |
|  | 0 | 3 | 17 | 1 | 4 | 16 |
|  | 0 | 4 | 18 | 0 | 3 | 15 |
|  | 0 | 4 | 14 | 0 | 3 | 18 |
|  | 0 | 3 | 16 | 0 | 3 | 18 |
| Average | 0 | 3 | 16 | 0 | 3 | 16 |
| Std dev | 0 | 1 | 2 | 0 | 1 | 2 |
| % CV | NA | 16% | 9% | 224% | 16% | 11% |

|  | Popcorn | | | Rice Bran Defatted | | |
|---|---|---|---|---|---|---|
|  | ND | 5 ppb | 20 ppb | ND | 5 ppb | 20 ppb |
|  | 0 | 5 | 25 | 1 | 3 | 15 |
|  | 0 | 5 | 23 | 0 | 3 | 15 |
|  | 1 | 5 | 20 | 1 | 3 | 14 |
|  | 1 | 5 | 21 | 1 | 3 | 14 |
|  | 0 | 5 | 19 | 1 | 4 | 17 |
| Average | 0 | 5 | 22 | 1 | 3 | 15 |
| Std dev | 1 | 0 | 2 | 0 | 0 | 1 |
| % CV | 137% | 0% | 11% | 56% | 14% | 8% |

|  | Rough Rice | | | Sorghum | | |
|---|---|---|---|---|---|---|
|  | ND | 5 ppb | 20 ppb | ND | 5 ppb | 20 ppb |
|  | 0 | 3 | 17 | 1 | 4 | 21 |
|  | 0 | 5 | 18 | 0 | 5 | 18 |
|  | 0 | 3 | 18 | 0 | 5 | 20 |
|  | 1 | 4 | 18 | 0 | 5 | 19 |
|  | 0 | 3 | 16 | 0 | 4 | 22 |
| Average | 0 | 4 | 17 | 0 | 4 | 20 |
| Std dev | 0 | 1 | 1 | 0 | 1 | 2 |
| % CV | 224% | 25% | 5% | 224% | 12% | 8% |

|  | Soybeans | | | Wheat | | |
|---|---|---|---|---|---|---|
|  | ND | 5 ppb | 20 ppb | ND | 5 ppb | 20 ppb |
|  | 0 | 6 | 19 | 0 | 3 | 16 |
|  | 0 | 4 | 16 | 0 | 4 | 18 |
|  | 0 | 5 | 17 | 0 | 4 | 16 |
|  | 0 | 4 | 18 | 0 | 3 | 15 |
|  | 0 | 4 | 17 | 0 | 4 | 16 |
| Average | 0 | 5 | 17 | 0 | 4 | 16 |
| Std dev | 0 | 1 | 1 | 0 | 1 | 1 |
| % CV | NA | 19% | 7% | NA | 15% | 7% |

Example 4: Fuminisin Extracted from Corn with Dry Bovine Serum Albumin

TABLE 20

FUMQ-WET-001
Samples: Naturally contaminated Corn Reference Material
Validated by HPLC. 10x of 10x Dilution from a 3x Extraction Ratio

| Conc ppb | Com# | T1 | T2 | C | RR Conc | Result | Recal |
|---|---|---|---|---|---|---|---|
| ND | 5 | 4494 | 4177 | 1083 | 0 | −6505 | 0 |
| NC | 5 | 4657 | 4110 | 1089 | 0 | −6589 | 0 |
| NC | 5 | 4923 | 4608 | 1365 | 0 | −6801 | 0 |
| NC | 5 | 4802 | 4526 | 1304 | 0 | −6720 | 0 |
| NC | AVE | 4719 | 4355 | 1210 | 0 | −6654 | 0 |
| NC | % CV | 4% | 6% | 12% | 0% | 2% | 0% |
| NC | % Inh/Pts | 100% | 100% | 100% | | 0 | |
| NC | | | | | | | |
| 540 | 5 | 3140 | 3634 | 1861 | 1 | −3052 | 600 |
| 500 | 5 | 3635 | 3985 | 2407 | 2 | −2806 | 650 |
| 500 | 5 | 3457 | 3931 | 2285 | 2 | −2818 | 650 |
| 500 | 5 | 3412 | 3826 | 2213 | 2 | −2812 | 650 |
| 500 | AVE | 3411 | 3844 | 2192 | 2 | −2872 | 638 |
| 500 | % CV | 6% | 4% | 11% | 29% | 4% | 4% |
| 500 | % Inh/Pts | 72% | 88% | 181% | | 3782 | |
| 500 | | | | | | | |
| 1040 | 5 | 3116 | 3557 | 2267 | 3 | −2139 | 950 |
| 1000 | 5 | 3101 | 3612 | 2412 | 3 | −1889 | 1000 |
| 1000 | 5 | 3182 | 3767 | 2583 | 3 | −1783 | 1100 |
| 1000 | | | | | | | |
| 1000 | AVE | 3133 | 3645 | 2421 | 3 | −1937 | 1017 |
| 1000 | % CV | 1% | 3% | 7% | 0% | 9% | 8% |
| 1000 | % Inh/Pts | 66% | 84% | 200% | | 4717 | |
| 1000 | | | | | | | |
| 2170 | 5 | 2625 | 3355 | 2686 | 6 | −608 | 1900 |
| 2000 | 5 | 2520 | 3187 | 2578 | 6 | −551 | 2000 |
| 2000 | 5 | 2260 | 2839 | 2245 | 6 | −609 | 1900 |
| 2000 | | | | | | | |
| 2000 | AVE | 2468 | 3127 | 2503 | 6 | −589 | 1933 |
| 2000 | % CV | 8% | 8% | 9% | 0% | 6% | 3% |
| 2000 | % Inh/Pts | 52% | 72% | 207% | | 6064 | |
| 2000 | | | | | | | |
| 4730 | 5 | 1850 | 2765 | 3206 | 18 | 1797 | 5700 |
| 5000 | 5 | 1971 | 2827 | 3201 | 16 | 1604 | 5300 |
| 5000 | 5 | 1987 | 2942 | 3218 | 16 | 1507 | 5000 |
| 5000 | | | | | | | |
| 5000 | AVE | 1936 | 2845 | 3208 | 17 | 1636 | 5333 |
| 5000 | % CV | 4% | 3% | 0% | 7% | 9% | 7% |
| 5000 | % Inh/Pts | 41% | 65% | 265% | | 8290 | |
| 5000 | | | | | | | |
| 1040 | 5 | 3414 | 3991 | 2596 | 2 | −2213 | 900 |
| 1000 | 5 | 3234 | 3728 | 2535 | 3 | −1892 | 1000 |
| 1000 | 5 | 3122 | 3676 | 2381 | 3 | −2036 | 1000 |
| 1000 | 5 | 3351 | 3966 | 2698 | 3 | −1921 | 1000 |
| 1000 | AVE | 3280 | 3840 | 2553 | 3 | −2016 | 975 |
| 1000 | % CV | 4% | 4% | 5% | 18% | 7% | 5% |
| 1000 | % Inh/Pts | 70% | 88% | 211% | | 4638 | |
| 1000 | | | | | | | |
| 2170 | 5 | 2675 | 3301 | 2668 | 6 | −640 | 1900 |
| 2000 | | 2731 | 3500 | 2756 | 6 | −719 | 1800 |
| 2000 | 5 | 2844 | 3598 | 2617 | 5 | −1208 | 1500 |
| 2000 | 5 | 2787 | 3525 | 2839 | 6 | −634 | 1900 |
| 2000 | AVE | 2759 | 3481 | 2720 | 6 | −800 | 1775 |
| 2000 | % CV | 3% | 4% | 4% | 9% | 34% | 11% |
| 2000 | % Inh/Pts | 58% | 80% | 225% | | 5854 | |
| 2000 | | | | | | | |
| 4730 | 5 | 2059 | 2992 | 3257 | 15 | 1463 | 4900 |
| 5000 | 5 | 1720 | 2614 | 2857 | 15 | 1380 | 4800 |
| 5000 | 5 | 1732 | 2521 | 2872 | 16 | 1491 | 5000 |
| 5000 | 5 | 1750 | 2633 | 2803 | 14 | 1223 | 4400 |
| 5000 | AVE | 1815 | 2690 | 2947 | 15 | 1389 | 4775 |
| 5000 | % CV | 9% | 8% | 7% | 5% | 9% | 6% |
| 5000 | % Inh/Pts | 38% | 62% | 244% | | 8043 | |
| 5000 | | | | | | | |
| 9460 | 5 | 1337 | 2231 | 3199 | 25 | 2830 | 8900 |
| 10000 | 5 | 1442 | 2457 | 3404 | 25 | 2909 | 9300 |
| 10000 | 5 | 1364 | 2409 | 3337 | 25 | 2901 | 9200 |
| 10000 | 5 | 1255 | 2186 | 3136 | 25 | 2831 | 9000 |
| 10000 | AVE | 1350 | 2321 | 3269 | 25 | 2868 | 9100 |
| 10000 | % CV | 6% | 6% | 4% | 0% | 2% | 2% |
| 10000 | % Inh/Pts | 29% | 53% | 270% | | 9522 | |
| 10000 | | Corrected by dilution factor | | | | | |
| 9460 | 5 | 2219 | 3021 | 4011 | 25 | 2782 | 8800 |
| 10000 | 5 | 1575 | 2204 | 3220 | 25 | 2661 | 8300 |

TABLE 20-continued

FUMQ-WET-001
Samples: Naturally contaminated Corn Reference Material
Validated by HPLC. 10x of 10x Dilution from a 3x Extraction Ratio

| Conc ppb | Com# | T1 | T2 | C | RR Conc | Result | Recal |
|---|---|---|---|---|---|---|---|
| 10000 | 5 | 2207 | 2887 | 4050 | 25 | 3006 | 9700 |
| 10000 | 5 | | | | | | |
| 10000 | AVE | 2000 | 2704 | 3760 | 25 | 2816 | 8933 |
| 10000 | % CV | 18% | 16% | 12% | 0% | 6% | 8% |
| 10000 | % Inh/Pts | 42% | 62% | 311% | | 9470 | |
| 10000 | | Corrected by dilution factor | | | | | |

Example 5: Zearalonone Extracted from Corn with Dry Bovine Serum Albumin

TABLE 21

ZEARQ-WET-001
Samples: Naturally contaminaed Corn Reference Material
Validated by HPLC. 10x of 10x Dilution from a 3x Extraction Ratio

| Conc | Com# | T1 | T2 | C | RR Conc | Result | Recal |
|---|---|---|---|---|---|---|---|
| ND | 5 | 4085 | 4054 | 1174 | 0 | −5791 | 14 |
| ND | 5 | 4531 | 4386 | 1165 | 0 | −6587 | 0 |
| ND | 5 | 4554 | 4349 | 1101 | 0 | −6701 | 0 |
| ND | 5 | 4921 | 4888 | 1507 | 0 | −6795 | 0 |
| ND | AVE | 4523 | 4419 | 1237 | 0 | −6469 | 4 |
| ND | % CV | 8% | 8% | 15% | 0% | 7% | 200% |
| ND | % Inh/Pts | 100% | 100% | 100% | | 0 | |
| ND | | | | | | | |
| 99 | 5 | 3474 | 3849 | 1970 | 11 | −3383 | 87 |
| 100 | 5 | 3590 | 3966 | 2264 | 17 | −3028 | 103 |
| 100 | 5 | 3482 | 3809 | 1966 | 11 | −3359 | 88 |
| 100 | 5 | 3476 | 3706 | 2081 | 17 | −3020 | 103 |
| 100 | AVE | 3506 | 3833 | 2070 | 14 | −3198 | 95 |
| 100 | % CV | 2% | 3% | 7% | 25% | 6% | 9% |
| 100 | % Inh/Pts | 78% | 87% | 167% | | 3271 | |
| 100 | | | | | | | |
| 254 | 5 | 2450 | 3110 | 2634 | 115 | −292 | 278 |
| 250 | 5 | 2926 | 3572 | 2888 | 91 | −722 | 242 |
| 250 | 5 | 2697 | 3388 | 2838 | 108 | −409 | 268 |
| 250 | 5 | 2658 | 3274 | 2664 | 97 | −604 | 252 |
| 250 | AVE | 2683 | 3336 | 2756 | 103 | −507 | 260 |
| 250 | % CV | 7% | 6% | 5% | 10% | 38% | 6% |
| 250 | % Inh/Pts | 59% | 75% | 223% | | 5962 | |
| 250 | | | | | | | |
| 1004 | 5 | 1178 | 2023 | 3630 | 892 | 4059 | 982 |
| 1000 | 5 | 1359 | 2420 | 4119 | 1064 | 4459 | 1094 |
| 1000 | 5 | 1127 | 1945 | 3417 | 782 | 3762 | 906 |
| 1000 | 5 | 1089 | 2121 | 3654 | 907 | 4098 | 992 |
| 1000 | AVE | 1188 | 2127 | 3705 | 911 | 4095 | 994 |
| 1000 | % CV | 10% | 10% | 8% | 13% | 7% | 8% |
| 1000 | % Inh/Pts | 26% | 48% | 300% | | 10563 | |
| 1000 | | | | | | | |
| ND | 5 | 4419 | 4197 | 1108 | 0 | −6400 | 1 |
| ND | 5 | 4328 | 3965 | 955 | 0 | −6383 | 1 |
| ND | 5 | 4250 | 4113 | 1234 | 0 | −5895 | 11 |
| ND | | | | | | | |
| ND | AVE | 4332 | 4092 | 1099 | 0 | −6226 | 4 |
| ND | % CV | 2% | 3% | 13% | 0% | 5% | 133% |
| ND | % Inh/Pts | 96% | 93% | 89% | | 243 | |
| ND | | | | | | | |
| 99 | 5 | 4124 | 4601 | 2781 | 1 | −3163 | 97 |
| 100 | 5 | 3628 | 3994 | 2176 | 1 | −3270 | 92 |
| 100 | 5 | 3687 | 4071 | 2166 | 1 | −3426 | 86 |
| 100 | | | | | | | |
| 100 | AVE | 3813 | 4222 | 2374 | 1 | −3286 | 92 |
| 100 | % CV | 7% | 8% | 15% | 0% | 4% | 6% |
| 100 | % Inh/Pts | 84% | 96% | 192% | | 3182 | |
| 100 | | | | | | | |
| 254 | 5 | 2911 | 3965 | 3277 | 7 | −322 | 276 |
| 250 | 5 | 2688 | 3361 | 2655 | 6 | −739 | 241 |

TABLE 21-continued

ZEARQ-WET-001
Samples: Naturally contaminaed Corn Reference Material
Validated by HPLC. 10x of 10x Dilution from a 3x Extraction Ratio

| Conc | Com# | T1 | T2 | C | RR Conc | Result | Recal |
|---|---|---|---|---|---|---|---|
| 250 | 5 | 2624 | 3439 | 2817 | 7 | −429 | 266 |
| 250 | | | | | | | |
| 250 | AVE | 2741 | 3588 | 2916 | 7 | −497 | 261 |
| 250 | % CV | 5% | 9% | 11% | 9% | 44% | 7% |
| 250 | % Inh/Pts | 61% | 81% | 236% | | 5972 | |
| 250 | | | | | | | |
| 1004 | 5 | 1182 | 2255 | 3740 | 25 | 4043 | 978 |
| 1000 | 5 | 1074 | 1818 | 3346 | 25 | 3800 | 915 |
| 1000 | 5 | 1214 | 2185 | 3594 | 25 | 3789 | 912 |
| 1000 | | | | | | | |
| 1000 | AVE | 1157 | 2086 | 3560 | 25 | 3877 | 935 |
| 1000 | % CV | 6% | 11% | 6% | 0% | 4% | 4% |
| 1000 | % Inh/Pts | 26% | 47% | 288% | | 10346 | |
| 1000 | | | | | | | |

The invention claimed is:

1. A method for extracting one or more mycotoxins from a dry test sample comprising the steps of:
   a) mixing the sample with a composition comprising a protein in water to form an admixture;
   b) separating said admixture between a settled layer and a distinct water layer comprising the one or more mycotoxins, and
   c) collecting at least a portion of said water layer, wherein said at least a portion of said water layer is an extract containing said one or more mycotoxins.

2. The method of claim 1, wherein, in said mixing step, said composition comprising a protein is dry and is mixed with the sample in water for form the admixture.

3. The method of claim 1, wherein the protein is an albumin.

4. The method of claim 3, wherein said albumin is bovine serum albumin.

5. The method of claim 3, wherein said albumin is porcine albumin.

6. The method of claim 1, wherein the protein is a collagen.

7. The method of claim 1, wherein the protein is a peptone.

8. The method of claim 7, wherein the protein is a gelatin.

9. The method of claim 7, wherein the protein is soy peptone.

10. The method of claim 1, wherein at least one of the one or more mycotoxins is fumonisin.

11. The method of claim 1, wherein at least one of the one or more mycotoxins is ochratoxin.

12. The method of claim 1, wherein at least one of the one or more mycotoxins is zearlanone.

13. The method of claim 1, wherein at least one of the one or more mycotoxins is aflatoxin.

14. The method of claim 1, wherein the test sample comprises a grain.

15. The method of claim 14, wherein the grain comprises corn.

16. The method of claim 14, wherein the grain comprises maize.

17. The method of claim 14, wherein the grain comprises distiller's grain.

18. The method of claim 14, wherein the grain comprises a rice.

19. The method of claim 1, wherein the composition comprising the protein is in the form of a tablet.

20. The method of claim 1, wherein the composition comprising the protein is in the form of a hydratable solid.

21. The method of claim 1, wherein the composition comprising the protein is in the form of a powder.

22. The method of claim 1, wherein the composition comprising the protein further comprises a preservative.

23. The method of claim 1, wherein the composition comprising the protein further comprises a biocide comprising 1.15% methylchloroisothizaolinone, 0.35% methylisothiazolinone, 23.00% $MgCl_2$ and $Mg(NO_3)_2$ in water.

24. The method of claim 1, wherein the composition comprising the protein further comprises a salt.

* * * * *